(12) United States Patent
Allen et al.

(10) Patent No.: US 6,353,476 B1
(45) Date of Patent: Mar. 5, 2002

(54) APPARATUS AND METHOD FOR SUBSTANTIALLY SIMULTANEOUS MEASUREMENT OF EMISSIONS

(75) Inventors: Fritz Schreyer Allen, Corrales; Danny S. Butterfield, Albuquerque, both of NM (US)

(73) Assignee: New Chromex, Inc., Albuquerque, NM (US)

( * ) Notice: Subject to any disclaimer, the term of this patent is extended or adjusted under 35 U.S.C. 154(b) by 0 days.

(21) Appl. No.: 09/603,547

(22) Filed: Jun. 26, 2000

Related U.S. Application Data

(63) Continuation-in-part of application No. 09/327,406, filed on Jun. 7, 1999, now abandoned.

(51) Int. Cl.[7] ................................................. G01J 3/44
(52) U.S. Cl. ...................................................... 356/301
(58) Field of Search ......................................... 356/301

(56) References Cited

U.S. PATENT DOCUMENTS 5,455,673 A * 10/1995 Alsmeyer et al. ........... 356/301
5,652,653 A * 7/1997 Alsmeyer et al. ........... 356/301

OTHER PUBLICATIONS

Vess et al., SPIE, vol. 1637, 1992, pp. 118–125.*

* cited by examiner

Primary Examiner—F. L. Evans
(74) Attorney, Agent, or Firm—Law Office of Ray R. Regan

(57) ABSTRACT

An apparatus and method for measuring an emission. A source of all excitation beam is provided. In the path of the excitation beam, means are located for providing one or more daughter beams. The one or more daughter beams are directed at one or more substances. The substances may include one or more known qualified substances, and one or more known unqualified substances. The substances have substantially similar characterizations. Positionable adjacent to the one or more substances are means for generating one or more emission beams. A spectral analysis device is provided for collecting spectral measurements substantially simultaneously from the one or more emission beams. Means are provided for subsequently comparing the spectral measurements from the one or more substances.

28 Claims, 2 Drawing Sheets

APPARATUS AND METHOD FOR SUBSTANTIALLY SIMULTANEOUS MEASUREMENT OF EMISSIONS

CROSS-REFERENCE TO RELATED APPLICATION

As required by 37 CFR 1.78, this application is a continuation-in-part of U.S. application Ser. No. 09/327,406, filed Jun. 7, 1999, now abandoned.

FEDERALLY SPONSORED RESEARCH AND DEVELOPMENT

Not Applicable.

FIELD OF THE INVENTION

The present invention pertains generally to the field of spectroscopy. More particularly, the present invention pertains to an apparatus that permits substantially simultaneous collection, and subsequent comparison, of one or more emissions from a plurality of radiation beams. The present invention is particularly, but not exclusively, useful for comparing spectral measurements from scattered emission beams from one or more known qualified substances and one or more unknown but qualified substances, having substantially similar characterizations.

BACKGROUND OF THE INVENTION

Spectroscopy is a general term for the process of measuring energy or intensity as a function of wavelength in a beam of light or radiation using an instrument generally referred to as a spectroscope. Many conventional spectroscopes, and components comprising a spectroscope system, also referred to as an instrument, may include features and components such as a slit through which radiation may pass, a collimator for producing a parallel beam of radiation, one or more prisms or gratings for dispersing radiation through differing angles of deviation based on wavelength, and components for viewing dispersed radiation. Spectroscopy uses absorption, emission, or scattering of electromagnetic radiation by atoms, molecules or ions to qualitatively and quantitatively study physical properties and processes of substances.

Light or radiation that during operation of a spectroscope system is to be directed at one or more substances may be referred to as excitation radiation. A beam of excitation radiation from a source of excitation radiation may be referred to as an excitation beam. As indicated, a spectroscopy instrument may include a number of components for directing, redirecting, dispersing, and modifying an excitation beam, including, without limitation, mirrors, gratings, wave guides, filters, lenses and similar components. An excitation beam may be directed at and through one or more of such components before being directed at selected substances.

Redirection of a radiation beam following contact with a substance commonly is referred to as scattering of radiation. To the extent that atoms or molecules in a substance absorb all or a portion of a beam of radiation, rather than reflect the radiation of an excitation beam, a substance may become excited, and the energy level of the substance may be increased to a higher energy level. Radiation that passes through a substance may produce a small portion of light that is scattered in a variety of directions. Radiation that is scattered but continues to have the same wavelength as the excitation radiation that contacted the substance may have the same energy, a condition often referred to as Rayleigh or elastically scattered light. Alternatively, radiation that is scattered during a change of vibrational state in molecules may be scattered with a different energy, and such scattered light is called Raman scattered light.

As regards Raman scattered light, a wave associated with electromagnetic radiation may be described by (i) wavelength, the physical length of one complete oscillation, and by (ii) frequency of the wave, the number of oscillations per second that pass a point. If radiation is directed at a substance, the wavelength of the radiation may remain substantially unchanged in scattered radiation. Alternatively, if radiation is directed at a substance, the wavelength in the scattered radiation may acquire one or more different wavelengths. The energy differential between the original radiation, and the scattered radiation, may be referred to as a Raman shift. The Raman shift is significant because spectroscopic measurement of Raman scattered light seeks to measure the resulting wavelength of such scattered light.

Raman phenomena are used in conjunction with spectroscopy to qualitatively and quantitatively study physical properties and processes of a substance, including without limitation, identification of chemical characterizations including, but not limited to, properties, compositions, and structures. The phenomenon of Raman scattered light, therefore, is useful in spectroscopy applications for studying qualities and quantities of physical properties and processes of substances, including identification of chemical properties, compositions, and structure of a substance. Raman shift spectroscopic analytical techniques are, therefore, applied to qualitative and quantitative studies of matter. If radiation is used to scatter light from a substance, and scattered radiation data is measured, the scattered radiation may provide one or more spectral data, including but not limited to frequencies associated with the substance, as well as the intensities of those shifted frequencies. The frequencies may be used to identify, without limitation, the chemical composition of the substance.

Merely identifying the chemical properties, composition, structure and other characterizations of a substance, however, is only one objective of use of Raman technology. Another objective of using the Raman phenomena in connection with spectroscopy is to rapidly obtain a high quality characterization of molecular matter. Raman spectroscopy frequently is used because Raman technology has the advantage of being nondestructive of physical matter being characterized. In addition, Raman technology requires minimal sample preparation, and often may provide information about an analyte although the analyte may be but a minor ingredient in a complex mixture or admixture of physical matter.

Although the qualitative capabilities of Raman technology have been recognized, providing and enhancing quantitative capabilities have remained challenging. A number of factors contribute to the lack of quantitative capabilities of Raman technology. For example, a single beam of radiation generally is used to implement Raman technology in connection with substance analyses. Conventional Raman experimentation often uses a source of incident radiation substantially monochromatic, preferably providing a single frequency or wavelength. Acceptance by those skilled in the art that the source of the excitation beam should be substantially monochromatic and provide a single frequency or wavelength has led to use of a variety of laser light sources as a source of excitation radiation. However, if an excitation beam changes frequency, the Raman shift calibration may be disturbed; if an excitation beam changes intensity, the Raman magnitude may change. Quantitative analysis also is complicated because, without the existence of a reference beam of radiation for comparison, instrumentation variabilities may affect the spectral shape of a Raman spectral measurement. A number of components of an instrument may contribute individually and collectively to undesirable instrumentation variabilities that affect spectral data measured by the instrument. Spectroscopic measurements of Raman scattered light, therefore, seeking to measure wavelength or intensities, or both, of scattered light, may be affected by the instrument, or spectroscopic system, itself.

While efforts have been introduced to compensate for these problems associated with quantitative Raman measurements, what still is needed is an apparatus that is independent of instrumentation variabilities, and has the capability of directly comparing one or more known qualified substances or materials with one or more known unqualified substances or materials whose spectral data have been collected simultaneously or substantially simultaneously.

Use of Raman technology would be enhanced if those and related problems were solved. At least one advantage of the novel present invention is that it provides an apparatus for substantially simultaneous collection of one or more emissions from a plurality of radiation beams. Another advantage of the present invention is the capability of the apparatus and method of the invention to compare spectral data and measurements from different beams from not only one or more known qualified substances, but also from one or more known unqualified substances, and to ascertain the similarity, or lack of similarity, between or among those substances having identical or substantially identical characterizations. As will be apparent to one skilled in the art, such an apparatus and method of operating the apparatus will achieve the objective and advantage of permitting direct comparison of Raman spectra of an known unqualified substance with a known qualified substance because the spectral data and measurements are collected substantially simultaneously, before comparison one with the other. Use of the same instrument in which the beams and spectral data are generated has the further advantage of attenuating or eliminating the effect of instrumentation variabilities on the spectral data. The ability of the present invention to substantially simultaneously collect spectral data measurements from one or more substances having substantially similar or substantially identical characterizations has important advantages over instruments currently available for conducting quality assurance and quality control, particularly where the objective is to verify that a measurement from a substance is similar to a known measurement from another qualified substance. An apparatus for substantially simultaneous measurement of one or more emissions from a radiation beam has the additional advantage of eliminating the need for a pre-established sample reference library.

At least one other advantage of the present invention, therefore, is elimination of the need to correct spectral data collected in connection with the substances. The instrument, which, as indicated, is often a spectrometer or its analog, need not be stabilized. Indeed, while Raman principles and phenomena are useful in operation of the invention, none of the Raman characteristics is determinative of the use and usefulness of the present invention. Raman characteristics are useful but not essential because an object of the invention is to compare spectral data of substances having substantially similar or identical characterizations. A number of other Raman apparatus and methods seek to correct spectral data to a true, correct or corrected, and relatively absolute standard. The present invention, however, does not seek to correct the spectral data, but only to compare spectral data.

Because the user seeks merely to compare data associated with substantially similar or substantially identical substances, means for comparison, including, but not limited to computer software programs, electronic hardware, or other devices useful in comparing or rationing data from multiple channels of an instrument, may be (i) quite simple in formulation, (ii) readily reprogrammed for a range of varying substances by the user of the present invention, and (iii) developed as decision-making programs, including merely "go-no go" or "yes-no" programs, or ratioing techniques for different information of the channels of the instrumentation components. Complicated or sophisticated algorithms or integral transforms used with Raman technology seeking to determine convolution functions, convolved spectra of substances being studied with the apparatus, or seeking to determine the standard Raman spectra of substances, are not required. The present invention, therefore, provides an inexpensive, simple, and cost-effective method and apparatus for comparing the spectral data of known unqualified substances with known qualified substances. While some Raman apparatus and methods provide for correction of instrumentation variabilities, the present invention does not require correction of instrumentation variabilities to achieve the advantages of the apparatus and method of the present invention.

Other presently available Raman apparatus and methods provide for simultaneously performing certain tasks during operation of the instrument. Simultaneity, however, of what is achieved by the present invention differs markedly from what may be achieved simultaneously by current apparatus. For example, at least one Raman instrument currently available simultaneously compensates Raman data for instrumentation variabilities. The present invention, however, as indicated, is not concerned with instrumentation variabilities. In addition, some currently available instruments provide for simultaneously interfacing radiation with a sample and a reference material, producing convolved spectra, and then adjusting the convolved spectra of the sample for the sole purpose of producing a standard Raman spectrum. That, too, is not an objective of the present invention. The present invention does not seek to determine standard Raman spectra, but to compare spectral data yielded from application of Raman technology. Raman radiation is used in connection with the present invention to assist in the determination of whether an known but unqualified substance is similar or identical to a known and qualified substance. Accordingly, the goal of the invention is not dependent on or affected by laser mode hops, calibration errors, thermal problems, and similar instrument variations.

Another salutary feature of the present invention is to reduce or eliminate sample preparation before operation of the apparatus and application of a method of use. The present invention presupposes that the substances to be compared share substantially similar or identical characterizations. Sample preparation, therefore, is irrelevant to the present invention.

Perhaps the most simplistic explanation of the advantages of the present invention is to consider the present invention's application in connection with composition of a substance. A variety of Raman apparatus are responsive to the question, "What is the composition of the sample?" Users of the present invention are not concerned with the composition of a substance per se. Instead, users of the present invention are interested in the answer to the question, "Is one substance the same as another substance?" As previously stated, a capability of the present invention includes determining the similarity, or lack of similarity, between or among one or more known qualified substances, and one or more known unqualified substances, having substantially similar or substantially identical characterizations. An alternative way to explicate the novelty of the present invention is to identify the substances whose characterizations are being compared as qualified and unqualified. A qualified substance, as contemplated by the present invention, has been tested to confirm that the qualified substance comports with a standard set of characterizations. An unqualified substance has not been tested, but is presumed to have substantially similar or identical characterizations as the qualified substance. Unqualified substances, for example, may be produced during a production or manufacturing process using means to produce one or more substances similar to or identical with a qualified substance, but not yet proven to be substantially similar to or identical with a qualified substance until compared with one another using the present invention. Accordingly, the present invention has application in a variety of fields. The present invention would be useful, for example, not only in quality control processes, but also in any environment requiring comparison of characteristics, including medical diagnostics.

By using Raman analyses optics and the apparatus provided by the present invention, which may include a multi-spatial channel detector, the instrument has the capabilities of a double or multiple beam instrument. The result is an inexpensive instrument, and inexpensive method for using the instrument for comparing substances by optical and mechanical comparison. Using such an instrument, a user is able to quickly determine by direct comparison whether one substance, a sample, for example, is within the specifications prescribed for the substance in general. The present invention, therefore, would be appropriate for QA/QC applications where the goal is to compare one or more known unqualified substances with one or more known qualified substances and other materials. A limiting problem in current applications of Raman technology is the frequency axis instability of sequential Raman measurements. The present invention, however, eliminates the problem by making measurements of substances that are similar or identical, collecting the measurements substantially simultaneously, and using the same instrument for making the measurements. In other words, the substances being compared have substantially similar sampling geometry.

These advantages and other objects and features of such an apparatus and method for substantially simultaneous measurement of an emission will become apparent to those skilled in the art when read in conjunction with the accompanying following description, drawing figures, and appended claims.

SUMMARY OF THE INVENTION

An apparatus and method for substantially simultaneous measurement of a emissions, according to the present invention, includes a source of an excitation beam. The source of an excitation beam may include a laser. The apparatus for substantially simultaneous measurement of a emissions also includes means locatable in the path of the excitation beam for providing one or more daughter beams. In addition, the present invention includes means in the path of one or more daughter beams for directing a daughter beam at one or more substances. The substances at which a daughter beam may be directed include substances whose physical properties and characteristics are unknown, as well as substances whose physical properties and characteristics are known, and have substantially similar or substantially identical characterizations.

The apparatus of the present invention also includes means adjacent the one or more substances, and locatable in the path of the one or more daughter beams, for generating one or more emission beams. An emission beam from a substance may be a Raman beam, and may include Raleigh scattered radiation as well as fluorescence. A spectral analysis device also is provided in connection with the present invention. The spectral analysis device also may be a multiple channel imaging spectrograph connectable to the emission beam generating means for collecting substantially simultaneously spectral measurements from the one or more emission beams. The spectral analysis device may be connected to the emission beam generating means. The present invention advances Raman technology in a variety of ways, including providing an apparatus for substantially simultaneously collecting spectral measurements from one or more emission beams and comparing the spectral measurements of one or more known unqualified substances with one or more known qualified substances. Accordingly, the spectral analysis device provided with the present invention may be an imaging spectrograph, one having multiple channels. By substantially simultaneously collecting spectral measurements or spectral data from one or more emission beams with the same instrument components, and by using emission beam generating means that are substantially identical, a number of problems are overcome that presently reduce the effectiveness of some qualitative and quantitative analyses using some Raman instruments. The present invention minimizes or eliminates qualitative measurement problems by providing an apparatus, and method of operating the apparatus, that is independent of instrumentation variabilities, and has the capability of directly comparing one or more known unqualified substances with one or more known qualified substances whose spectral data have been collected simultaneously, or substantially simultaneously, with the same instrument. The spectral analysis device of the present invention, therefore, is capable of collecting substantially simultaneously spectral measurements from each of the emission beams by substantially simultaneously receiving emission beams for measurement. Problems associated with sequential measurements are eliminated. In addition, the device for generating emission beams are substantially identical in physical components, construction, and assembly. The present invention also includes means combinable with the spectral analysis device for comparing the spectral measurement from the emission beams using means well known in the art.

The advantages of the present invention are achieved by use of instrument structural components in a different manner than instruments currently are used in connection with Raman technology. The need to correct spectral data collected in connection with the substances is unnecessary. The instrument of the present invention need not be stabilized. None of the Raman characteristics such as wavelength and frequency is important because spectral data of substantially similar substances are compared. The present invention does not seek to correct spectral data, but only to compare spectral data. The present invention, however, does not require correction of instrumentation variabilities.

What is achieved simultaneously using the present invention differs significantly from what may be achieved simultaneously using other Raman instruments. For example, at least one Raman instrument currently available compensates for instrumentation variabilities. Comparisons between and among known and unknown substances is accomplished.

This eliminates instrumentation variabilities as a concern. The present invention is not concerned with obtaining an absolute Raman spectrum. Raman radiation is used in connection with the present invention to assist in the determination of whether one an unknown but qualified substance is similar or identical to a known qualified substance. Accordingly, the goal of the invention is not dependent on or affected by laser mode hops, calibration errors, thermal problems, and similar instrument variations. A useful feature of the present invention is reduction or elimination of sample preparation before operation of the apparatus and application of a method of use because the substances to be compared share substantially similar or identical characterizations.

The foregoing has outlined broadly the more important features of the invention to better understand the detailed description which follows, and to better understand the contribution of the present invention to the art. Before explaining at least one embodiment of the invention in detail, it is to be understood that the invention is not limited in application to the details of construction, and to the arrangements of the components, provided in the following description or drawing figures. The invention is capable of other embodiments, and of being practiced and carried out in various ways. Also, the phraseology and terminology employed in this disclosure are for purpose of description, and should not be regarded as limiting.

As those skilled in the art will appreciate, the conception on which this disclosure is based may be used as a basis for designing other structures, cooperation of structure, methods, and systems for carrying out the purposes of the present invention. The claims, therefore, include such equivalent constructions. Further, the abstract associated with this disclosure is neither intended to define the invention, which is measured by the claims, nor intended to be limiting as to the scope of the invention.

The novel features of this invention, and the invention itself, both as to structure and operation, are best understood from the accompanying drawing, considered in connection with the accompanying description of the drawing, in which similar reference characters refer to similar parts, and in which:

DESCRIPTION OF THE PREFERRED EMBODIMENTS

Figure 1:
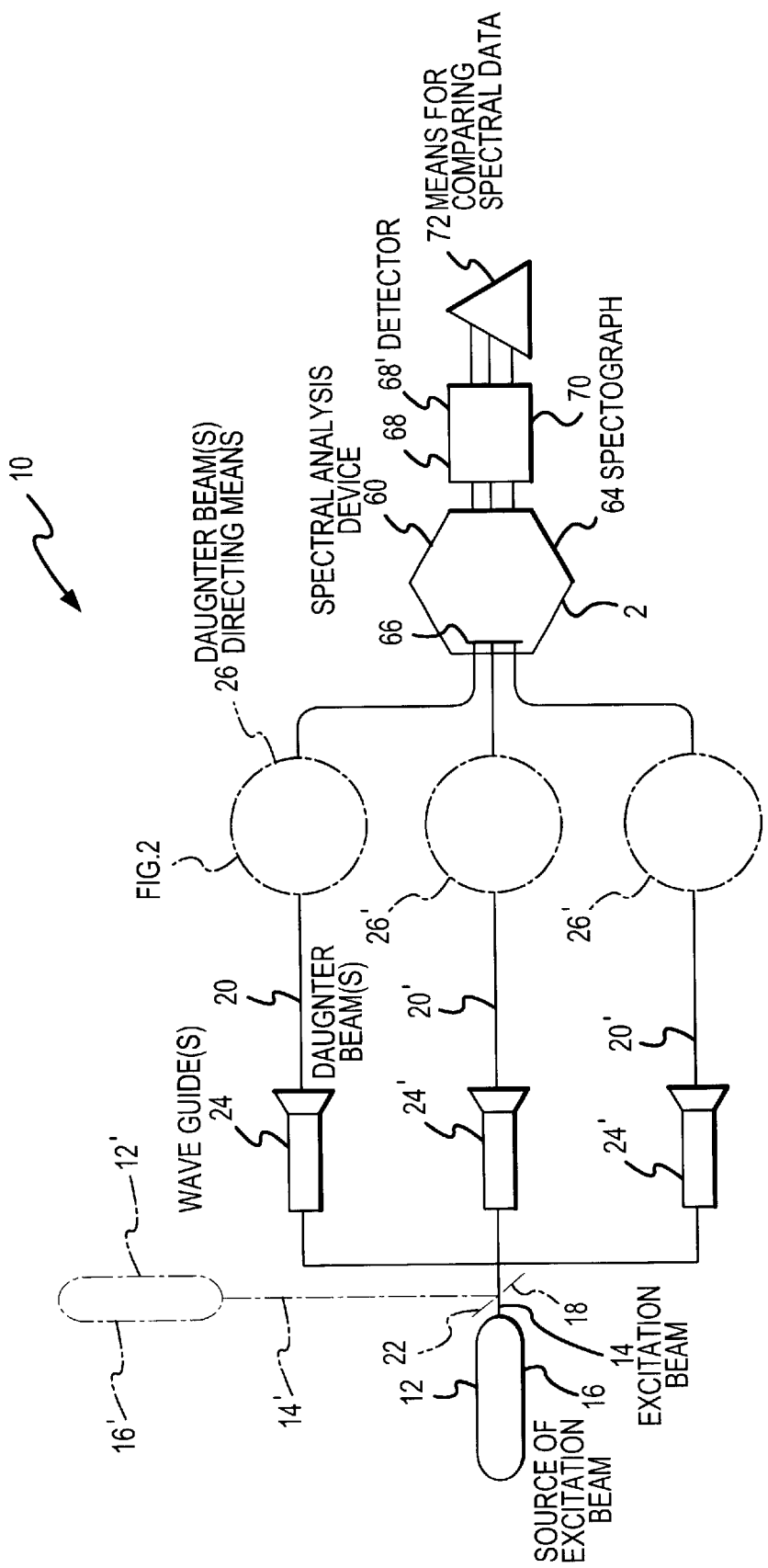
FIG. 1 is a schematic drawing of the apparatus for measuring an emission as provided by the present invention.

Referring initially to FIG. 1, an apparatus for measuring an emission according to the present invention is shown and generally designated 10. As shown, the apparatus for measuring an emission includes a source 12 of an excitation beam 14. Source 12 of excitation beam 14 provides excitation radiation in the form of substantially monochromatic radiation or light. Source 12 of excitation beam 14, therefore, may be a laser 16. A variety of laser light sources may be used as a laser in connection with the present invention not only because of the substantially monochromatic nature of the radiation from laser 16, but also because of the high intensity of radiation from laser 16. Gas lasers such as helium-neon, helium-cadmium, argon-ion, krypton-ion, as well as solid state lasers such as Nd-YAG, and diode lasers, solid state tunable lasers, liquid dye lasers, and other lasers are suitable for use as laser 16 in connection with the present invention. In addition, laser 16 used as source 12 of excitation beam 14 may be a diode laser. The diode laser may but need not be frequency stabilized. Laser 16 also may include multi-mode characteristics. In another alternative embodiment of the present invention, source 12 of excitation beam 14 may be a single mode laser that is frequency stable. In yet another embodiment, source 12 of excitation beam 14 may be other than a laser 16.

As also shown in FIG. 1, an apparatus for measuring an emission 10, according to the present invention, includes means 18 locatable in the path of excitation beam 14 for providing one or more daughter beams 20. Means 18 locatable in the path of excitation beam 14 for providing one or more daughter beams 20 may include one or more beam splitter wave guides 22. As is well known to those skilled in the art, fibers of ultra-pure glass, having a central core of higher refractive-index glass than the outer cladding, capable of conducting modulated light signals by total internal reflection, may be used either as a conduit or wave guide to direct a beam of radiation from a transmitter, in this situation daughter beam 20, to another receiver or target. In a preferred embodiment of the present invention, therefore, one or more fiber optic wave guides 24 is included for directing the one or more daughter beams 20 through the apparatus for measuring an emission 10. In another embodiment of the present invention, one or more daughter beams 20 may be directed into substance 28 by direct coupled means, such that light signals may be directed to a target such as substance 28 directly, without an intermediate device such as one or more fiber optic wave guides 24

Figure 2:
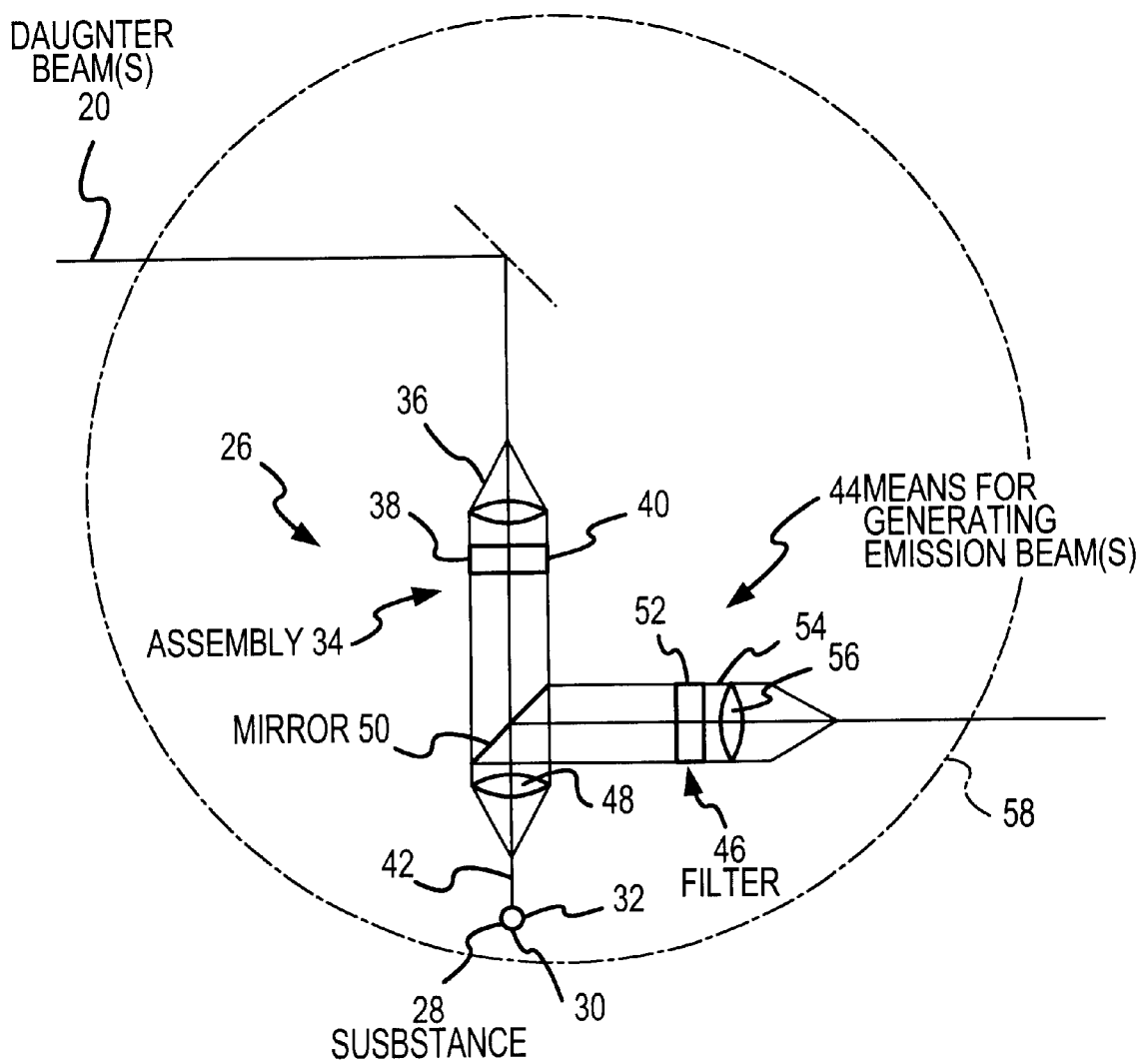
FIG. 2 is a schematic drawing of a device shown in FIG. 1 for generating an emission beam.

In addition, as shown in FIG. 1, but perhaps best shown in FIG. 2, the present invention includes means 26 in the path of the one or more daughter beams 20 for directing a daughter beam 20 at one or more substances 28. Substance 28 may include a known qualified substance 30. Substance 28 may also be an known unqualified substance 32 whose properties and characteristics are determined by the present invention. Means 26 for directing daughter beam 20 at one or more substances 28 may include a variety of components for directing, redirecting, dispersing, and modifying one more excitation beams 14, including, without limitation, mirrors, gratings, wave guides, filters, lenses and similar components assembled as assembly 34 for directing daughter beam 20 at the one or more substances 28. As shown in FIG. 2, daughter beam 20 may be directed at and through one or more of such components before being directed at selected physical matter such as the one or more substances 28. In a preferred embodiment of the present invention, each assembly 34 for directing daughter beam 20 at one or more substances 28 is preferably substantially identical in composition, arrangement, and properties. Assembly 34 for directing daughter beam 20 at one or more substances 28 preferably includes a first lens 36. First lens 36 has the capability of collimating daughter beam 20 emerging from fiber optic wave guide 24. Assembly 34 therefore has the capability to obtain from daughter beam 20 a parallel or near parallel beam of radiation from daughter beam 20 by redirecting photons of light as the photons of light pass through first lens 36. As also shown best in FIG. 2, daughter beam 20, in a preferred embodiment of the present invention, after passing through first lens 36, is directed to a filter 38 of assembly 34. Preferably, filter 38 of assembly 34 is a band-pass filter 40. Band-pass filter 40 is capable of freely passing radiation having frequencies within specified limits. As used in the present invention, band-pass filter 40 may be used to remove silica Raman from daughter beam 20. In another embodiment of the present invention, direct coupling of daughter beam 20 to substance 28 would eliminate the need for band-pass filter 40 or similar intermediary devices.

In the field of Raman technology, it is known that redirection of a radiation beam following contact with a substance 28 may be scattered. Redirection of a radiation beam following contact with substance 28 may produce one or more emission beams 42. To the extent that atoms or molecules in known qualified substance 30 or known unqualified substance 32 absorb all or a portion of daughter beam 20, rather than reflect radiation in daughter beam 20, known qualified substance 30 or known unqualified substance 32 may become excited. If excited, the energy level of known qualified substance 30 or known unqualified substance 32 may be increased to a higher energy level. Radiation from daughter beam 20 that passes through known qualified substance 30 or known unqualified substance 32, rather than be reflected, may produce a portion of light, usually comparatively small, that is scattered in a variety of directions. Radiation that is scattered but continues to have the same wavelength as the radiation that contacted known qualified substance 30 or known unqualified substance 32 may retain the same energy level that the radiation originally had, a condition often referred to as Rayleigh or elastically scattered light. Alternatively, radiation that is scattered during a change of vibrational state in molecules may be scattered with a different energy level. Such scattered light may be called Raman scattered light. The energy differential between the original radiation and the scattered radiation may be referred to as a Raman shift. The Raman shift is significant because a spectroscopic measurement of Raman scattered light seeks to measure the resulting wavelength of such scattered light.

Accordingly, an apparatus for measuring an emission 10, according to the present invention, includes means 44 adjacent one or more substances 28 for generating one or more emission beams 42. As perhaps best shown in FIG. 2, in a preferred embodiment of the present invention, the term "adjacent" is not limited to abutting or touching one or more substances 28, but means located close to, or in the general vicinity of, one or more substances 28. Means 44 for generating one or more emission beams 42 may include a number of components for generating, directing, redirecting, dispersing, or modifying one or more emission beams 42, including, without limitation, mirrors, gratings, wave guides, filters, lenses and similar components assembled as device 46 for generating one or more emissions beams 42. In a preferred embodiment of the present invention, each device 46 for generating one or more emission beams 42 is substantially identical in composition, arrangement and properties. Preferably, device 46 for generating one or more emission beams 42 includes a second lens 48. Second lens 48 has the capability of collimating one or more emissions 42, including obtaining from emission beam 42 a parallel or near parallel beam of radiation by distributing photons of light as the photons of light pass through second lens 48. Second lens 48 also has the capability of focusing daughter beam 20 onto the target such as substance 28. Emission beam 42, in a preferred embodiment of the present invention, as best shown in FIG. 2, may also be directed to a dichroic mirror 50. Emission beam 42 also may be directed to a second filter 52. In a preferred embodiment of the present invention, second filter 52 is a long-pass filter 54. Long-pass filter 54 is selected for use in connection with the present invention for selective enhancement of emission beam 42. The present invention also may include a third lens 56 through which emission beam 42 passes after exiting long-pass filter 54. Third lens 56 has the capability of focusing emission beam 42. In an alternative embodiment of the present invention, means 26 locatable in the path of one or more daughter beams 20 for directing one or more daughter beams 20 at one or more substances 28, and means 46 positionable adjacent one or more substances 28 for generating one or more emission beams 42, may be a distally filtered fiber optic probe head 58.

As shown in FIG. 1, a spectral analysis device 60 also is provided in connection with the present invention. In a preferred embodiment of the present invention, spectral analysis device 60 is connectable to one or more devices 26 for generating an emission beam 42. At least one objective of using the Raman phenomena in connection with spectroscopy is to rapidly obtain a high quality characterization of molecular matter, such as known qualified substance 30 or known unqualified substance 32. Raman spectroscopy is used because Raman technology has the advantage of being nondestructive of the physical matter being characterized. In addition, use of the present invention requires minimal preparation of known qualified substance 30, and often may provide information about an analyte although the analyte may be but a minor ingredient in a complex mixture or admixture of physical matter. The present invention advances Raman technology in part by providing an apparatus for measuring an emission 10 that substantially simultaneously collects spectral measurements from one or more emission beams 42 from one or more substances and comparing the spectral measurements . Spectral analysis device 60 used in connection with the present invention, therefore, is preferably a spectrograph 62. Spectrograph 62 is a spectroscopy instrument designed for use over a wide range of frequencies. Spectrograph 62 preferably records spectral data electronically. In a preferred embodiment of the present invention, spectrograph 62 is an imaging spectrograph 64. One or more emissions beams 42 may be collected by imaging spectrograph 64 at different positions on the entrance slit 66 of imaging spectrograph 64. Collection of one or more emission beams 42 at different positions on entrance slit 66 of imaging spectrograph 64, in the preferred embodiment of the present invention, is achieved by selective placement of a fiber optic receiver (not shown).

Imaging spectrograph 64 preferably also includes a multiple channel detector 68, as shown schematically in FIG. 1. Multiple channel detector 68 will receive spectral dispersion associated with the one or more emission beams 42 in one dimension, and will separate channels for each emission beam 42 in a second dimension. Typically, the spectral dimension will be horizontal, and the one or more spatial channels will be vertical, when recorded on multiple channel detector 68. Pixel tracks on multiple channel detector 68, corresponding to one or more spatial channels, can be accumulated vertically and displayed as spectral data for each such channel. Charge coupled detectors may have multi-channel capabilities, allowing a charge coupled detector to accept spectra substantially simultaneously, or substantially at one point in time. Accordingly, a charge coupled detector 70 is used in the preferred embodiment of the present invention.

While preferably each daughter beam 20 has the same or substantially similar energy levels, residual differences may be compensated for by nulling spectral signals for identical substances. The same charge coupled detector 70 also may display spectral data of one or more emission beams 42 on a channel comprised of a band of pixels. Multiple channel detector 68 may be, as a nonexclusive example, a photo diode array detector 68'. The channels, which may be one or more bands of pixels on charge coupled detector 70, will record spatial spectral data collected by spectral analysis device 60. The spectral data may be displayed on any of a variety of display devices well known in the art, including a screen of a computer if included with the means for comparing the spectral data 72. In another embodiment of the present invention, spectral data may not be displayed, but instead a simple indicator may be used to indicate that the channel readings are the same.

By substantially simultaneously collecting spectral measurements from one or more emission beams 42 within the same instrument, and using emission beam generating means 46 that are substantially identical, a number of problems are overcome that affect analyses using Raman technology, particularly quantitative analyses. As will be evident to one skilled in the art, instrumentation variabilities will affect one or more sets of spectral data comparability. Spectral data may be manipulated mathematically and compared rapidly to ascertain if the spectral data of known unqualified substance 32 is within the specification of known qualified substance 30. Some currently available Raman technology devices cannot directly compare or differentiate spectral data because of the frequency axis instability induced by Raman measurements collected sequentially rather than substantially simultaneously. Collecting spectral data substantially simultaneously attenuates or eliminates the problem of frequency axis instability. Because spectral data analysis is made directly from substantially simultaneously collected spectral data, the data analysis is simplified. The present invention also includes means 72 combinable with the spectral analysis device for comparing the spectral measurement from the emission beams, generally using mathematical formulae well known in the art. The present invention therefore may adjust for shifts, or variations, in the spectral data collected.

While the apparatus and method for measurement of emissions 10 shown in the drawing figures is one embodiment of the present invention, it is merely one embodiment of the invention, is not intended to be exclusive, and is not a limitation of the present invention. The particular apparatus for substantially simultaneous measurement of one or more emissions from a plurality of radiation beams as shown and disclosed in detail in this instrument is fully capable of obtaining the objects and providing the advantages stated, but this disclosure is merely illustrative of the presently preferred embodiments of the invention, and no limitations are intended in connection with the details of construction, design or composition other than as provided and described in the appended claims.

What is claimed is:

1. An apparatus for substantially simultaneous measurement of emissions, comprising:
    a source of an excitation beam;
    means locateable in the path of the excitation beam for providing at least two daughter beams;
    means locateable in the path of the at least two daughter beams for directing the one or more daughter beams at one or more substances having substantially similar characterizations;
    means positionable adjacent the one or more substances for generating at least two emission beams;
    a spectral analysis device connectable to the emission beam generating means for substantially simultaneously collecting spectral data from the at least two emission beams; and
    means for comparing the spectral data of the at least two emissions beams with each other.

2. An apparatus for substantially simultaneous measurement of emissions as recited in claim 1, wherein the source of the excitation beam is a laser.

3. An apparatus for substantially simultaneous measurement of emissions as recited in claim 1, wherein the daughter beams providing means includes one or more beam splitter waveguides.

4. An apparatus for substantially simultaneous measurement of emissions as recited in claim 1, wherein the one or more substances includes a known qualified material.

5. An apparatus for substantially simultaneous measurement of emissions as recited in claim 1, wherein the one or more substances includes a known unqualified material.

6. An apparatus for substantially simultaneous measurement of emissions as recited in claim 1, wherein the at least two emission beam generating means are substantially identical.

7. An apparatus for substantially simultaneous measurement of emissions as recited in claim 1, wherein the spectral analysis device includes means for substantially simultaneously receiving the at least two emission beams.

8. An apparatus for substantially simultaneous measurement of emissions as recited in claim 1, wherein the at least two emission beams are a Raman beam.

9. An apparatus for substantially simultaneous measurement of emissions as recited in claim 1, wherein the at least two emission beams includes an induced emission.

10. An apparatus for substantially simultaneous measurement of emissions as recited in claim 1, wherein the at least two emission beams includes Raleigh scattered radiation.

11. An apparatus for substantially simultaneous measurement of emissions as recited in claim 1, wherein the spectral analysis device is an imaging spectrograph.

12. An apparatus for substantially simultaneous measurement of emissions as recited in claim 1, wherein the spectral analysis device includes a plurality of channels.

13. An apparatus for substantially simultaneous measurement of emissions as recited in claim 1, wherein the comparing means include a computer.

14. An apparatus for comparison of one or more emissions from a plurality of radiation beams, comprising:
    a source of an excitation beam;
    means locateable in the path of the excitation beam for providing a plurality of daughter beams;
    means locateable in the path of the plurality of daughter beams for directing one or more of the plurality of daughter beams at one or more known qualified substances having substantially identical characterizations;
    means locateable in the path of the plurality of daughter beams for directing one or more of the plurality of daughter beams at one or more known unqualified substances having substantially identical characterizations;
    means positionable adjacent the one or more qualified substances and the one or more unqualified substances for generating emission beams from the one or more known qualified substances and the one more known unqualified substances;
    a multiple channel imaging spectrograph connectable to the emission beam generating means for collecting substantially simultaneously spectral measurements from the one or more emissions beams; and
    means combinable with the multiple channel imaging spectrograph for comparing the one or more emission beams from the one or more known qualified substances with the one or more emission beams from the one or more known unqualified substances.

15. An apparatus for comparison of one or more emissions from a plurality of radiation beams as recited in claim 14, wherein the source of the excitation beam is substantially monochromatic.

16. An apparatus for comparison of one or more emissions from a plurality of radiation beams as recited in claim 15, wherein the source of the excitation beam is a laser.

17. An apparatus for comparison of one or more emissions from a plurality of radiation beams as recited in claim 14, wherein the emission beam generating means are substantially identical.

18. An apparatus for comparison of one or more emissions from a plurality of radiation beams as recited in claim 14, wherein the multiple channel imaging spectrograph includes means for receiving substantially simultaneously the one or more emission beams.

19. An apparatus for comparison of one or more emissions from a plurality of radiation beams as recited in claim 14, wherein the one or more emission beams is a Raman beam.

20. An apparatus for comparison of one or more emissions from a plurality of radiation beams as recited in claim 14, wherein the one or more emission beams includes Raleigh scattered radiation.

21. An apparatus for comparison of one or more emissions from a plurality of radiation beams as recited in claim 14, wherein the one or more emission beams includes fluorescence.

22. An apparatus for comparison of one or more emissions from a plurality of radiation beams as recited in claim 14, wherein the comparing means includes means for mathematically comparing the spectral measurements.

23. A method for measuring emissions from a plurality of radiation beams, comprising the steps of:

selecting one or more sources of an excitation beam;

installing in the path of an excitation beam means for providing two or more daughter beams;

including in the path of the two or more daughter beams means for directing the two or more daughter beams at one or more known qualified substances having substantially similar characterizations to the two or more daughter beams;

including in the path of the two or more daughter beams means for directing the two or more daughter beams at one or more known unqualified substances having substantially similar characterizations to the two or more daughter beams;

providing means adjacent the one or more known qualified substances and one or more known unqualified substances for generating at least one emission beam;

furnishing a spectral analysis device connectable to the emission beam generating means for collecting substantially simultaneously spectral data from each of the at least one emission beam; and using means combinable with the spectral analysis device for comparing the spectral data from the emission beam from the one or more known qualified substances and from the one or more known unqualified substances.

24. A method for measuring emissions from a plurality of radiation beams as recited in claim 23, wherein the selecting step includes the substep of selecting a laser.

25. A method for measuring emissions from a plurality of radiation beams as recited in claim 24, wherein the installing step includes the substep of installing a beam splitter wave guide.

26. A method for comparing emissions from a plurality of radiation beams as recited in claim 25, wherein the providing step includes the substeps of:

a. providing one or more lenses;

b. providing one or more filters; and c. providing one or more mirrors.

27. A method for comparing emissions from a plurality of radiation beams as recited in claim 26, wherein the step of furnishing a spectral analysis device includes the substeps of:

a. furnishing one or more optical channels; and b. furnishing one or more optical input members for collecting spectral measurements from the one or more emission beams from the one or more known qualified substances and one or more known unqualified substances.

28. A method for comparing emissions from a plurality of radiation beams as recited in claim 27, wherein the using step includes the substeps of:

a. adjusting the spectral measurements; and b. using mathematical means for comparing the spectral measurements.

* * * * *